(12) United States Patent
Yokoyama et al.

(10) Patent No.: US 7,902,333 B2
(45) Date of Patent: Mar. 8, 2011

(54) LABELING METHODS WITH OXYGEN ISOTOPES

(75) Inventors: Shigeyuki Yokoyama, Yokohama (JP);
Kazuhiko Yamada, Yokohama (JP);
Toshio Yamazaki, Yokohama (JP)

(73) Assignee: Riken, Saitama (JP)

( * ) Notice: Subject to any disclaimer, the term of this patent is extended or adjusted under 35 U.S.C. 154(b) by 585 days.

(21) Appl. No.: 11/597,058

(22) PCT Filed: May 20, 2005

(86) PCT No.: PCT/JP2005/009240
§ 371 (c)(1),
(2), (4) Date: Nov. 20, 2006

(87) PCT Pub. No.: WO2005/113471
PCT Pub. Date: Dec. 1, 2005

(65) Prior Publication Data
US 2008/0206820 A1 Aug. 28, 2008

(30) Foreign Application Priority Data
May 21, 2004 (JP) .................................. 2004-151506

(51) Int. Cl.
*C07K 14/00* (2006.01)
*A61B 5/055* (2006.01)
*C07H 21/04* (2006.01)
(52) U.S. Cl. .......................... 530/350; 424/9.3; 536/23.1
(58) Field of Classification Search .................. None
See application file for complete search history.

(56) References Cited
OTHER PUBLICATIONS

Fuller, JC Jr. et al., "Use of 18O-labelled leucine and phenylalanine to measure protein turnover in muscle cell cultures and possible futile cycling during aminoacylation", Biochem J. 294(Pt 2): 427-433 (1993).*
Ponnusamy, E. et al., "Synthesis of 17O isotope labeled Leu-enkephalin and 17O n.m.r.", (Int. J. Pept. Protein Res. 32(1): 21-27 (Jul. 1988); Abstract only).*
Jones, John, Amino Acid and Peptide Synthesis, Oxford 2nd Ed., 2002, p. 35.
Gerothanassis, et al., $^{17}$O NMR Chemical Shifts of the Twenty Protein Amino Acids in Aqueous Solution, Magnetic Resonance in Chemistry, vol. 23, No. 8, 1985, pp. 659-665.
Ponnusamy et al., Synthesis of Oxygen-17 Labeled Thyrotropin Releasing Hormone, Journal of Labelled Compounds and Radiopharmaceuticals, 1985, vol. 22, No. 11, pp. 1135-1141.
Kabalka, G.W., et al., "[17]O Enrichment Methods," $^{17}$O NMR Spectroscopy in Organic Chemistry, pp. 28-29, (1991).
Steinschneider et al., International Journal of Applied Radiation and Isotopes, 1981, vol. 32, No. 2, pp. 120-121.
Steinschneider et al., International Journal of Peptide & Protein Research, 1981, vol. 18, No. 3, pp. 324-333.
Ponnusamy et al., Journal of Labelled Compounds and Radiopharmaceuticals, 1987, vol. 24, No. 7, pp. 773-778.

* cited by examiner

*Primary Examiner* — Anand U Desai
(74) *Attorney, Agent, or Firm* — Birch, Stewart, Kolasch & Birch, LLP

(57) ABSTRACT

The present invention provides methods for labeling One or two oxygen atom(s) in a carboxyl group of a carboxyl-containing compound with an oxygen isotope selected from oxygen-17 ($^{17}$O) or oxygen-18 ($^{18}$O). The methods of the present invention are characterized in that an activated ester of the carboxyl-containing compound (carboxylic acid) is reacted with $H_2^{17}O$ or $H_2^{18}O$ in the presence of an activator. In the methods of the present invention, the reaction between the activated ester of a carboxylic acid and $H_2^{17}O$ or $H_2^{18}O$ can be allowed to proceed without including drastic conditions such as strongly acidic conditions or alkaline hydrolysis because an activator is used.

12 Claims, 3 Drawing Sheets

Mass spectra of unlabeled and labeled dipeptides Ala-Val $^{17}O$ MAS NMR spectroscopy of Ile[$^{17}O$]

a 14 minutes  18 minutes b 14 minutes

LABELING METHODS WITH OXYGEN ISOTOPES

TECHNICAL FIELD

The present application is based on the Japanese Patent Application No. 2004-151506 filed on May 21, 2004.

The present invention relates to methods for labeling a compound having a carboxyl group with an oxygen isotope selected from oxygen-17 ($^{17}O$) or oxygen-18 ($^{18}O$). The methods of the present invention are characterized in that an activator is used.

BACKGROUND ART

Nuclear Magnetic Resonance (NMR) is a resonance method for structural analysis using atomic nuclei. This method observes resonance spectra of individual atomic nuclei, so that even atoms having similar electron cloud sizes can be distinctly differentiated from each other. Studies of structural analysis by NMR using $^1H$, $^{13}C$ and $^{15}N$ are under way.

Biological components, especially amino acids are important components capable of forming proteins, and analyses of the high-order structures of many proteins using NMR are being reported as well as elucidation of their biological functions. Oxygen atoms are very important in biological components such as amino acids and sugars, but $^{17}O$ NMR spectroscopy has not been sufficiently developed. One reason for this is that the natural abundance of the isotope $^{17}O$ is as low as 0.038%. See Table 1 summarizing the properties of atomic nuclei of hydrogen, carbon, nitrogen and oxygen that can be used in NMR.

TABLE 1

| Element | Nuclide | Isotopic abundance (atomic percentage)[a] | Spin | NMR resonant frequency (MHz)[b] | Note |
|---|---|---|---|---|---|
| Hydrogen | $^1H$ | 99.985 | ½ | 100.000 | |
| | $^2H$ | 0.015 | 1 | 15.351 | |
| | $^3H$ | — | ½ | 106.663 | Radioisotope (half life 12.26 years) |
| Carbon | $^{12}C$ | 98.90 | 0 | — | |
| | $^{13}C$ | 1.10 | ½ | 25.144 | |
| Nitrogen | $^{14}N$ | 99.634 | 1 | 7.224 | |
| | $^{15}N$ | 0.366 | ½ | 10.133 | |
| Oxygen | $^{16}O$ | 99.762 | 0 | — | |
| | $^{17}O$ | 0.038 | 5/2 | 13.557 | |
| | $^{18}O$ | 0.200 | 0 | — | |

[a]IUPAC Inorganic Chemistry Division, CAWIA SIAM: Isotopic Compositions of the elements 1989. Pure Appl. Chem., 63, 991(1991); Chemistry and Industry, Vol. 48, April (1995).
[b]Resonant frequency in a static magnetic field of 2.35 tesla.

As shown in Table 1, the natural abundance of $^{17}O$ is also significantly low as compared with $^{13}C$ (1.10%) and $^{15}N$ (0.366%). Thus, test compounds to be analyzed by $^{17}O$ NMR must be artificially enriched in $^{17}O$ by labeling oxygen atoms in the test compounds with $^{17}O$.

Carboxyl-containing compounds such as amino acids can be enriched in $^{17}O$ by reacting the amino acids with $H_2^{17}O$ to replace an oxygen atom in the carboxyl group by $^{17}O$. However, such exchange reaction hardly proceeds spontaneously, so that it must be forced to proceed by using a catalyst or the like. Prior to the present invention, the reaction was performed under strongly acidic conditions by saturating $H_2^{17}O$ with hydrogen chloride gas (Non-Patent Publication: No. 4), or the carboxyl group was preliminarily subjected to alkyl esterification and then alkaline hydrolysis using sodium hydroxide (Non-Patent Publications: Nos. 2, 3, 5), etc. However, these conventional conditions involved the following problems: the exchange reaction of the carboxyl group under acidic conditions invited degradation of tryptophan, cysteine, asparagine and glutamine, and alkaline hydrolysis of alkyl ester derivatives inevitably caused racemization of optically active amino acids.

Thus, there have been demands for a method for labeling carboxyl-containing compounds with oxygen isotopes such as oxygen-17 ($^{17}O$) under milder conditions.

REFERENCES

Non-Patent Publication: No. 1: John Jones, Amino Acid and Peptide Synthesis, p. 35;
Non-Patent Publication: No. 2: W. Boykin, 17O NMR Spectroscopy in Organic Chemistry, p. 28-29;
Non-Patent Publication: No. 3: Steinschneider et al., International Journal of Applied Radiation & Isotopes, 32, 120-121 (1981);
Non-Patent Publication: No. 4: Steinschneider et al., International Journal of Peptide Protein Research, 18, 324-333 (1981);
Non-Patent Publication: No. 5: I. P. Gerothanassis et al., Magnetic Resonance in Chemistry, 23, 659-665 (1985).

DISCLOSURE OF THE INVENTION

Problems to be Solved by the Invention

An object of the present invention is to provide a novel method for labeling one or two oxygen atom(s) in a carboxyl group of a carboxyl-containing compound with an oxygen isotope selected from oxygen-17 ($^{17}O$) or oxygen-18 ($^{18}O$). The method of the present invention is characterized in that an activated ester of the carboxyl-containing compound (carboxylic acid) is reacted with $H_2^{17}O$ or $H_2^{18}O$ in the presence of an activator.

In an embodiment of the present invention, the activator is preferably a coupling reagent or reaction-promoting additive in peptide synthesis. Alternatively, the activator is preferably a triazole derivative or tetraalkyluronium derivative.

In the present invention, the activated carboxylic acid ester is preferably an ester selected from pentafluorophenyl esters, paranitrophenyl esters, 2,4,6-trichlorophenyl esters, and N-hydroxysuccinimide esters.

Another object of the present invention is to provide a carboxyl-containing compound labeled with an oxygen isotope selected from oxygen-17 ($^{17}O$) or oxygen-18 ($^{18}O$) by the method of the present invention.

Still another object of the present invention is to provide a process for preparing a synthetic peptide labeled with an oxygen isotope selected from oxygen-17 ($^{17}O$) or oxygen-18 ($^{18}O$) at the oxygen atom in the peptide bond. The process of the present invention comprises:

1) reacting an activated ester of an amino acid with $H_2^{17}O$ or $H_2^{18}O$ in the presence of an activator; and
2) reacting the carboxyl group in the labeled amino acid with the N-terminal amino group of an amino acid or peptide bound to a solid phase.

Still another object of the present invention is to provide a synthetic peptide labeled with an oxygen isotope selected from oxygen-17 ($^{17}O$) or oxygen-18 ($^{18}O$) at the oxygen atom in the peptide bond, prepared by the process of the present invention.

Still another object of the present invention is to provide a process for preparing a labeled amino acid labeled with an oxygen isotope selected from oxygen-17 ($^{17}O$) or oxygen-18 ($^{18}O$) at one or two oxygen atom(s) in the carboxyl group. The process of the present invention comprises:

1) reacting an activated ester of an amino acid protected with a protecting group at a terminal amino group with $H_2^{17}O$ or $H_2^{18}O$ in the presence of an activator; and 2) removing the protecting group from the resulting labeled amino acid having the protecting group.

Still another object of the present invention is to provide a use of a labeled amino acid prepared by the process of the present invention for cell-free or living cell-based protein synthesis.

Means to Solve the Problems

Labeling Methods with Oxygen Isotopes

The present invention provides a method for labeling one or two oxygen atom(s) in a carboxyl group of a carboxyl-containing compound with an oxygen isotope selected from oxygen-17 ($^{17}O$) or oxygen-18 ($^{18}O$). The method of the present invention is characterized in that an activated ester of the carboxyl-containing compound (carboxylic acid) is reacted with $H_2^{17}O$ or $H_2^{18}O$ in the presence of an activator. An embodiment of the labeling method of the present invention with oxygen-17 ($^{17}O$) is explained below by way of example, but the present invention can also be equally applied as a labeling method with oxygen-18($^{18}O$). As used herein, the expression "oxygen-17 ($^{17}O$)" means to include oxygen isotope(s) "oxygen-17 ($^{17}O$) and/or oxygen-18 ($^{18}O$)" unless otherwise specified. Moreover, the expression "$H_2^{17}O$" means to include "$H_2^{17}O$ and/or $H_2^{18}O$", unless otherwise specified.

(1) Activators

The carboxyl-containing compound can be enriched in $^{17}O$ by reacting the carboxyl-containing compound with $H_2^{17}O$ to replace an oxygen atom in a carboxyl group by $^{17}O$. However, such exchange reaction hardly proceeds spontaneously. Thus, the present invention is characterized in that the carboxyl group is reacted as an activated ester with $H_2^{17}O$ in the presence of an activator in order to promote the reaction.

In an embodiment of the present invention, the activator is preferably a coupling reagent or reaction-promoting additive in peptide synthesis. Alternatively, the activator is preferably a triazole derivative or tetraalkyluronium derivative. The coupling reagent or reaction-promoting additive in peptide synthesis means a substance acting to promote the reaction during amide bond formation in peptide synthesis or catalyzing or promoting the formation of an activated ester of an amino acid used as a starting material for peptide synthesis.

Coupling reagents or reaction-promoting additives in peptide synthesis include, e.g., triazole derivatives, tetraalkyluronium derivatives, etc.

Triazole derivatives and tetraalkyluronium derivatives (e.g., tetramethyluronium derivatives) have functions of coupling reagents, reaction-promoting additives, etc. in peptide synthesis.

Examples of preferred activators specifically include, but not limited to, 1-hydroxy-1H-benzotriazole (CAS 2592-95-2), 6-chloro-1-hydroxy-1H-benzotriazole (CAS 26189-19-6), 3-hydroxy-3H-1,2,3-triazolo[4,5-b]pyridine (CAS 39968-33-7), (1H-benzotriazol-1-yloxy)tris (dimethylamino)phosphonium hexafluorophosphate (CAS 56602-33-6), (1H-benzotriazol-1-yloxy) trispyrrolidinophosphonium hexafluorophosphate (CAS 128625-52-5), 2-(1H-benzotriazol-1-yl)-1,1,3,3-tetramethyluronium hexafluorophosphate (CAS 94790-37-1), 2-(1H-benzotriazol-1-yl)-1,1,3,3-tetramethyluronium tetrafluoroborate (CAS 125700-67-6), 2-(6-chloro-1H-benzotriazol-1-yl)-1,1,3,3-tetramethyluronium hexafluorophosphate (CAS 330645-87-9), 2-(6-chloro-1H-benzotriazol-1-yl)-1,1,3,3-tetramethyluronium tetrafluoroborate (CAS 330641-16-2), 2-(3H-1,2,3-triazolo[4,5-b]pyridin-3-yl)-1,1,3,3-tetramethyluronium hexafluorophosphate (CAS 148893-10-1), 2-(cyano(ethoxycarbonyl)methyleneamino)-1,1,3,3-tetramethyluronium tetrafluoroborate (CAS 136849-72-4), 2-succinimidyl-1,1,3,3-tetramethyluronium tetrafluoroborate, etc.

Preferred is 1-hydroxy-1H-benzotriazole or 6-chloro-1-hydroxy-1H-benzotriazole. Most preferred is 1-hydroxy-1H-benzotriazole (CAS 2592-95-2), e.g. commercially available from Novabiochem (Darmstadt, Germany).

The activator is preferably used at a 0.1 to 100-fold molar excess, most preferably 1 to 10-fold molar excess relative to the activated carboxylic acid ester.

(2) Activated Carboxylic Acid Esters

In the present invention, the carboxyl group is preferably activated by esterification in order to promote the reaction with $H_2^{17}O$. Activated esters include, but not limited to, pentafluorophenyl esters, paranitrophenyl esters, 2,4,6-trichlorophenyl esters, N-hydroxysuccinimide esters, cyanomethyl esters, etc. Preferred are pentafluorophenyl esters or N-hydroxysuccinimide esters. These activated esters are known as useful esters for activating amino acids during solid-phase peptide synthesis (Non-Patent Publication: No. 1).

In the present invention, the carboxyl group to be labeled with an oxygen isotope such as oxygen-17 is preferably a carboxyl group in a biological component or a biological component-related molecule selected from the group consisting of amino acids, peptides, proteins, sugars, oligosaccharides, polysaccharides, glycoproteins, fatty acids, lipids, glycolipids, proteoglycans, cholesterols and steroids. These biological components or biological component-related molecules often play important biological functions in living bodies, and therefore, the determination of their high-order structures by $^{17}O$ NMR is also useful for the elucidation of their biological functions.

The method of the present invention can be used to label an oxygen in the carboxyl group in an amino acid or the oxygen in the amide bond in a peptide or protein with oxygen-17. Alternatively, the method of the present invention can also be applied to label an oxygen atom in the side chain carboxyl group in an amino acid or in an amino acid residue in a peptide or protein. When the side chain carboxyl group and $H_2^{17}O$ are reacted in the presence of an activator, only an oxygen atom at specific site can be specifically labeled by preliminarily protecting other functional groups than the target side chain carboxyl group with a protecting group.

The method of the present invention can also be used to label an oxygen atom in the carboxyl group in a glycosyl residue in a sugar, oligosaccharide or polysaccharide. The carboxyl group labeled with oxygen-17 may be a free carboxyl group or may form a carboxylic acid ester after labeling.

The method of the present invention can also be used to label an oxygen atom in a carboxyl group in a complex carbohydrate selected from glycoproteins, glycolipids and proteoglycans. Glycoproteins are proteins having a carbohydrate attached thereto via an asparagine residue (N-linked glycoproteins) or a serine or threonine residue (O-linked glycoproteins) in the proteins. Glycolipids are lipids such as sphingosine having a carbohydrate attached thereto. Proteoglycans are glycoprotein complexes containing a glycosaminoglycan (GAG) chain that is a carbohydrate having a repeating disaccharide unit containing a sulfated carbohydrate or a uronic acid. All these complex carbohydrates are well known to those skilled in the art.

The labeling method of the present invention can also be used to label other biological components or biological component-related molecules such as fatty acids, lipids, cholesterols and steroids, etc.

The activated carboxylic acid ester that can be used in the labeling method of the present invention is preferably an activated ester of an amino acid. That is, the carboxyl group to be labeled with oxygen-17 is preferably a carboxyl group in an amino acid, peptide or protein. When an activated ester of the carboxyl group in an amino acid, peptide or protein is reacted with $H_2^{17}O$ in the presence of an activator, the amino group in the amino acid, or the terminal amino group or side chain amino group in the peptide or protein should be preliminarily protected with a protecting group.

The protecting group for the amino group is preferably selected from the group consisting of 9-fluorenylmethoxycarbonyl (Fmoc), t-butyloxycarbonyl (Boc), benzyloxycarbonyl (Cbz) and 4-methoxybenzyloxycarbonyl (MeOCBz) groups. These protecting groups are generally known as protecting groups for the amino groups of free amino acids during solid-phase peptide synthesis. These protecting groups may be removed by known methods depending on the types of the protecting groups after the labeling reaction with oxygen-17. For example, the Fmoc protecting group can be preferably removed with ease by treating it with piperidine at room temperature for several hours. Fmoc-L-amino acids or their pentafluorophenyl esters are commercially available from e.g., Novabiochem (Darmstadt, Germany) or can be prepared by synthesizing the Fmoc-amino acid pentafluorophenyl esters from their corresponding Fmoc-amino acids and pentafluorophenol.

(3) Labeling Methods of the Present Invention

The method of the present invention is performed by reacting an activated ester of a carboxyl-containing compound (carboxylic acid) with $H_2^{17}O$ in the presence of an activator. The reaction between the activated ester of a carboxyl-containing compound (carboxylic acid) and $H_2^{17}O$ is preferably performed for, but not limited to, 1 hour to 10 days, more preferably 1 hour to 10 hours preferably at room temperature to 50° C., more preferably room temperature. The reaction mixture is preferably stirred.

The exchange reaction between an oxygen atom in the carboxyl group and $^{17}O$ should be forced to proceed using a catalyst or the like because it hardly proceeds spontaneously. Prior to the present invention, the reaction was performed under strongly acidic conditions by saturating $H_2^{17}O$ with hydrogen chloride gas (Non-Patent Publication: No. 4), or the carboxyl group was preliminarily subjected to alkyl esterification and then alkaline hydrolysis using sodium hydroxide (Non-Patent Publications: Nos. 2, 3, 5), etc. However, these conventional conditions involved the following problems: the exchange reaction of the carboxyl group under acidic conditions invited degradation of tryptophan, cysteine, asparagine and glutamine, and alkaline hydrolysis of alkyl esterification products inevitably caused racemization of optically active amino acids.

In the present invention, the reaction between the activated ester of a carboxylic acid and $H_2^{17}O$ can rapidly proceed under mild conditions at room temperature by using a suitable activator without including drastic conditions such as strongly acidic conditions or alkaline hydrolysis. For example, when the carboxyl group to be labeled with an oxygen isotope is a carboxyl group in an amino acid, peptide or protein and the amino group in the amino acid or the terminal amino group or side chain amino group in the peptide or protein is protected with a protecting group such as a 9-fluorenylmethoxycarbonyl group, the amino acid or amino acid residue can be inhibited from degradation and racemization (Example 4). In the labeling method of the present invention, inhibition of side reactions and inhibition of racemization or isomerization are also required for labeling other carboxyl-containing biological components or biological component-related molecules.

The method of the present invention made it possible to efficiently label an oxygen atom in a carboxyl group with oxygen-17 under mild reaction conditions. In the method of the present invention, the percentage at which at least one oxygen atom in a carboxyl group is labeled or the labeling rate depends on the labeling rate of the $H_2^{17}O$-enriched water used, and theoretically the upper limit is the labeling rate of the $H_2^{17}O$-enriched water used in the case of single labeling. As shown in Examples 1 and 2 herein, the percentage at which at least one oxygen atom in the carboxyl group in Fmoc-Ala was labeled with $H_2^{17}O$-enriched water having a labeling rate of 20.3% was 20.9% (Table 3).

In the reaction of the present invention, water containing $H_2^{17}O$ is practically used. The proportion of $H_2^{17}O$ contained in water used for the reaction is not limited. In the examples below, water containing 20.3% of $H_2^{17}O$ was used for the reaction in view of the cost. The labeling rate of $^{17}O$ increases with the proportion of $H_2^{17}O$ though it is very expensive. In Example 2, the percentage at which at least one oxygen atom was labeled was 20.9%, which explains that the reaction of the labeling method of the present invention can completely proceed as theoretically expected. The $H_2^{17}O$ solution used in the labeling method of the present invention can be recovered after use and repeatedly used.

The labeling method of the present invention also comprises repeating the steps for labeling described above. That is, an embodiment comprising: (1) reacting an activated ester of a carboxylic acid with $H_2^{17}O$ (or $H_2^{18}O$) in the presence of an activator; (2) converting the resulting $^{17}O$-labeled carboxylic acid into an activated ester; (3) further reacting the resulting activated ester of the carboxylic acid with $H_2^{17}O$ (or $H_2^{18}O$) in the presence of an activator; and then (4) repeating the steps (1)-(3) is also included within the scope of the present invention. By repeating the labeling steps, the percentage at which at least one oxygen atom in the carboxyl group is labeled increases and two oxygen atoms in the carboxyl group may be simultaneously labeled.

Oxygen isotopes include $^{18}O$ in addition to $^{17}O$. The method of the present invention can also be applied to label carboxyl groups with $^{18}O$. Materials labeled with oxygen-18 ($^{18}O$) are expected for use as medical tracers or the like.

Compounds Labeled with Oxygen Isotopes

The method of the present invention made it possible to label a carboxyl group with an oxygen isotope (oxygen-17 ($^{17}O$) and/or oxygen-18 ($^{18}O$)) under mild conditions by using an activator. Thus, the method of the present invention made it possible to label even compounds that could not be virtually labeled with oxygen isotopes under conventional drastic reaction conditions. Therefore, carboxyl-containing compounds labeled with an oxygen isotope by the labeling method of the present invention are also included in the present invention.

The carboxyl-containing compounds of the present invention are preferably selected from the group consisting of, e.g., amino acids, peptides, proteins, sugars, oligosaccharides, polysaccharides, glycoproteins, fatty acids, lipids, glycolipids, proteoglycans, cholesterols and steroids.

Compounds containing a carboxyl group labeled with $^{17}O$ by the method of the present invention are useful for structural analysis by $^{17}O$ NMR, for example. As shown in Table 1, $^{17}O$ has a spin of 5/2 and its nucleus is in the form of a positively charged spheroid. It is generally difficult to measure NMR spectra of $^{17}O$ because the signal width is broadened by the interaction between the electronic quadrupole moment reflecting ellipsoidal nuclear charge distribution and the electric field gradient. However, the problem with the electronic quadrupole moment can be somewhat improved by using solid-state NMR instead of solution NMR.

Processes for Preparing Synthetic Peptides Labeled with Oxygen Isotopes

The present invention also provides a process for preparing a synthetic peptide labeled with an oxygen isotope selected from oxygen-17 ($^{17}O$) or oxygen-18 ($^{18}O$) at the oxygen atom in the peptide bond. A labeled synthetic peptide can be prepared by labeling an amino acid by the labeling method of the present invention and using the amino acid for solid-phase peptide synthesis.

Methods for solid-phase peptide synthesis are not specifically limited, but known methods can be used. Thus, an embodiment of the process for preparing a synthetic peptide of the present invention comprises:

1) reacting an activated ester of an amino acid with $H_2^{17}O$ or $H_2^{18}O$ in the presence of an activator; and
2) reacting the carboxyl group in the labeled amino acid with the N-terminal amino group of an amino acid or peptide bound to a solid phase.

Alternatively, a free carboxyl group in the C-terminus or side chain in a synthetic peptide can be labeled by using the method of the present invention.

The present invention also provides a synthetic peptide labeled with an oxygen isotope selected from oxygen-17 ($^{17}O$) or oxygen-18 ($^{18}O$) at the oxygen atom in the peptide bond, prepared by the process of the present invention.

Processes for Preparing Amino Acids Labeled with Oxygen Isotopes

The present invention also aims to provide a process for preparing a labeled amino acid labeled with an oxygen isotope selected from oxygen-17 ($^{17}O$) or oxygen-18 ($^{18}O$) at one or two oxygen atom(s) in the carboxyl group. The process of the present invention comprises:

1) reacting an activated ester of an amino acid protected with a protecting group at a terminal amino group with $H_2^{17}O$ or $H_2^{18}O$ in the presence of an activator; and
2) removing the protecting group from the resulting labeled amino acid having the protecting group.

The process of the present invention can be applied to prepare any natural or non-natural amino acid. The activated ester of an amino acid is as generally described in the section of "Labeling methods with oxygen isotopes (2) activated carboxylic acid esters" herein above. The protecting group for the amino group and the method for removing it are also as described above.

The present invention also provides a use of the labeled amino acid prepared by the process of the present invention for cell-free or living cell-based protein synthesis. Cell-free or living cell-based protein synthesis systems are well known to those skilled in the art. For example, a cell-free protein synthesis system includes cell extracts, a DNA or RNA encoding the target protein, amino acids, energy sources, buffers, etc. Living cell-based protein synthesis systems involve culturing transformed cells of a microorganism such as *E. coli* or yeast or animal cells in a medium containing amino acids or the like to synthesize a protein. Labeled amino acids prepared by the process of the present invention can be used to synthesize proteins labeled with oxygen isotopes in any protein synthesis system.

BRIEF EXPLANATION OF THE DRAWINGS

FIG. 1a and FIG. 1b show the results of the unlabeled dipeptide and the $^{17}O$-labeled dipeptide, respectively.

EXAMPLES

Figure 1:
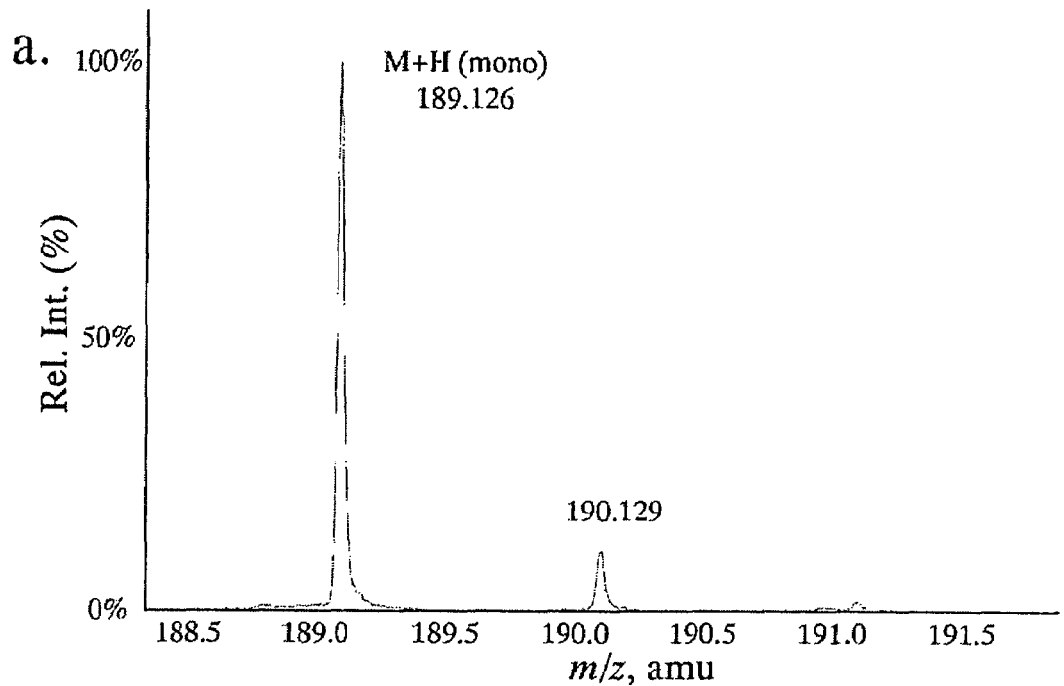
FIG. 1 shows mass spectra of unlabeled and labeled dipeptides Ala-Val. The ordinates show relative abundance (Rel.Int) (%). The abscissas show m/z in atomic mass unit.
Figure 1:
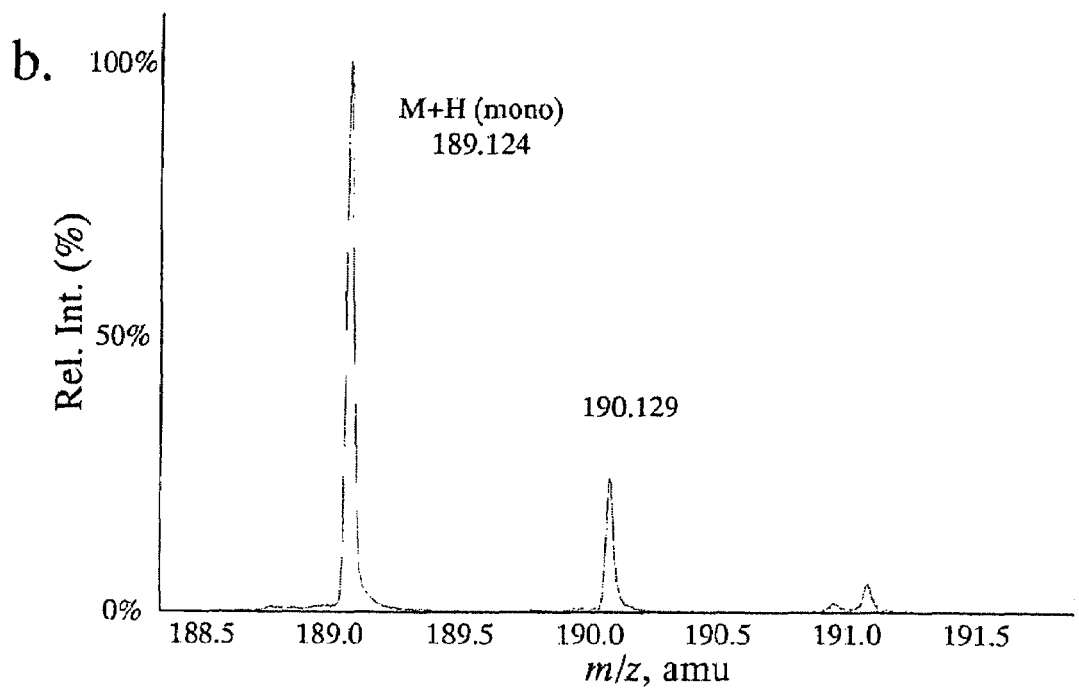

The following examples further illustrate the present invention but are not intended to limit the technical scope of the invention. Those skilled in the art can readily add modifications/changes to the present invention on the basis of the description herein, and such modifications/changes are included in the technical scope of the present invention.

Example 1

Synthesis of $^{17}O$-labeled Fmoc-amino Acids, $^{17}O$-labeled Peptides and $^{17}O$-labeled Free Amino Acids (1) Materials Water containing $H_2^{17}O$ was purchased from Nippon Sanso Corporation (Tokyo, Japan). Pentafluorophenyl esters of Fmoc-L-amino acids, Wang resin for Fmoc-L-amino acids, and anhydrous N-hydroxybenzotriazole (HOBt) were purchased from Novabiochem (Darmstadt, Germany) and used without further purification. A SepPak® Plus $C_{18}$ cartridge was purchased from Waters Corporation (Milford, Mass., U.S.A).

(2) Synthesis of $^{17}O$-enriched Fmoc-amino acids

As an example, the introduction of a $^{17}O$ label into the carboxyl group of Fmoc-L-valine is described in detail below.

Under $N_2$ gas, 1.523 g of Fmoc-L-valine pentafluorophenyl ester and 421 mg of anhydrous HOBt were dissolved in 4.0 mL of THF, and immediately after then, 500 µL of $H_2^{17}O$-enriched water (labeling rate 20.3%) was added to the solution. The mixture was stirred at room temperature for 10 days. The reaction was occasionally monitored by $^1H$ NMR. After the reaction has been completed, the solvent was evaporated to dryness under reduced pressure to give a white product. An excess of the $H_2^{17}O$ solution containing THF was recovered for use in the next run.

The crude product was purified by chromatography on silica gel (100:1 (v/v) ethyl acetate:acetic acid) to give 791 mg of Fmoc-L-valine [$^{17}O$]. The results of solution NMR and mass spectrometry of this product agreed with the calculated values.

Fmoc-L-alanine[$^{17}$O] was also prepared by a similar procedure.

The procedure described above can be in principle applied to all amino acids constituting proteins.

(3) Solid-phase Synthesis of $^{17}$O-labeled Peptides

The $^{17}$O-enriched Fmoc-protected amino acids synthesized in (2) can be directly used for the synthesis of $^{17}$O-enriched peptides. Dipeptides containing the $^{17}$O-enriched alanine component ALA[$^{17}$O]-ALA and ALA[$^{17}$O]-VAL were synthesized by solid-phase peptide synthesis on Wang resin. A synthetic procedure of ALA[$^{17}$O]-VAL is described below.

A reaction tube was charged with 685 mg of Fmoc-L-valine attached to Wang resin, and washed with anhydrous DMF. The product bound to the resin was treated with 5.0 mL of a piperidine/DMF (2:8) solution. The mixed solution was shaken for about 1 hour, and the solvent was removed by filtration.

Under nitrogen, 191 mg of $^{17}$O-enriched Fmoc-L-alanine and 90 mg of anhydrous HOBt were dissolved in 4.0 mL of anhydrous DMF. Then, 98 µL of N,N'-diisopropylcarbodiimide was added to the amino acid solution. Reaction was allowed to proceed at room temperature for about 1 hour.

L-valine bound to the Wang resin was treated with the amino acid solution containing $^{17}$O-enriched Fmoc-L-alanine in the reaction tube, and the mixture was slowly shaken for 3 days. The solvent was removed by filtration, and then the resin was treated with 5.0 mL of a piperidine/DMF (2:8) solution. The resin was washed with anhydrous DMF, isopropyl alcohol and anhydrous dichloromethane. Then, the resin was suspended in a 95% aqueous TFA solution for 3 hours. The resin was removed by filtration. The filtrate was collected in a flask, and the solvent was evaporated to dryness. Thus, 143 mg of a crude product was obtained, and the generation of ALA-VAL was confirmed by $^1$H NMR.

(4) Synthesis of $^{17}$O-enriched Free Amino Acids $^{17}$O-enriched free L-amino acids can be readily obtained by removing the protecting group from $^{17}$O-enriched Fmoc L-amino acids. As a typical experimental example, 250 mg of $^{17}$O-enriched Fmoc-L-valine was treated with 5.0 mL of a piperidine/DMF (2:8) solution at room temperature for several hours, and the solvent was evaporated under reduced pressure. The residue was dissolved in distilled water and purified through a SepPak® Plus C$_{18}$ cartridge to give 101 mg of free $^{17}$O-valine. The generation of L-valine was confirmed by solution $^1$H NMR.

If the protecting group is attached to the side chain of the amino acid, a step for cleaving the side chain protecting group is required before or after removing the Fmoc-protecting group.

Example 2

Labeling Rates with $^{17}$O in an Amino Acid (Fmoc-Ala) and a Dipeptide (Ala-Val)

Object

In the present example, the labeling rates with $^{17}$O in the $^{17}$O-labeled amino acid (Fmoc-Ala) and dipeptide (Ala-Val) of the present invention prepared in Example 1 are evaluated. The labeling rates were determined by using the peak areas of the first isotopic peak and the second isotopic peak in the labeled products in ESI-MS (electrospray ionization mass spectrometry).

Test Samples

*Fmoc-Ala ($C_{18}H_{17}NO_4$); 311.1157478 Da (exact mass) unlabeled and labeled with $^{17}$O.
*Ala-Val ($C_8H_{16}N_2O_3$); 188.1160823 Da (exact mass) unlabeled and labeled with $^{17}$O.

These molecular weights were calculated on the basis of $^{12}$C:12, $^1$H:1.007825, $^{14}$N:14.003074, $^{16}$O:15.994915, $^{18}$O: 17.99916 (as described Dictionary of Physics and Chemistry, p. 1532).

Method (1) A dried sample was dissolved in 50% acetonitrile.

(2) The solution was diluted as appropriate with a 50% acetonitrile solution containing 0.1% formic acid.

(3) A 50% acetonitrile solvent containing 0.1% formic acid was delivered to MS at 5 µl/min via an HPLC pump, and 1 µl of the diluted sample from (2) was applied. ESI-MS measurements were performed in the positive ion mode over the m/z range 100-1000. Five measurements were performed for each of Fmoc-Ala unlabeled and labeled with $^{17}$O, and Ala-Val unlabeled and labeled with $^{17}$O.

Results

As a result of the measurements in the positive ion mode, mass-related ion peaks could be observed. FIG. 1 shows mass spectra of the unlabeled and labeled dipeptides Ala-Val. The peak areas of hydrogen adduct peaks in the mass spectra were used to analyze the labeling rates.

Specifically, $^{17}$O was assumed as a novel isotope element X and the abundance ratio of the isotope was established as shown in Table 2 below.

TABLE 2

| | Abundance ratios (%) of isotopes of various elements | | | | |
|---|---|---|---|---|---|
| | C | H | N | O | X ($^{17}$O) |
| 1$^{st}$ | 98.90 | 99.985 | 99.634 | 99.762 | 99.8-x |
| 2$^{nd}$ | 1.10 | 0.015 | 0.366 | 0.038 | x |

For example, the labeling rate x of $^{17}$O-labeled Ala-Val was calculated for $C_8H_{16}N_2O_2X$ from the area ratio between the first isotopic peak (m/z: 189.124 in FIG. 1b) and the second isotopic peak (m/z: 190.129 in FIG. 1b) found from the mass spectrum as follows.

[Formula 1]
Example) Calculation method for labeled Ala-Val Calculation was performed for $C_8H_{17}N_2O_2X$ by using the actual peak area ratio.

8×[natural isotopic abundance of $^{13}$C (1.10)/natural isotopic abundance of $^{12}$C (98.90)]

+17×[natural isotopic abundance of $^2$H (0.015)/natural isotopic abundance of $^1$H (99.985)]

+2×[natural isotopic abundance of $^{17}$O (0.038)/natural isotopic abundance of $^{16}$O (99.762)]

+1×[labeling rate of $^{17}$X (x)/unlabeling rate of $^{16}$X (99.8-x)]

+2×[natural isotopic abundance of $^{15}$N (0.366)/natural isotopic abundance of $^{14}$N (99.634)]

=0.099637851+x/(99.8-x)

=23.762/100.

X=12.1%

Fmoc-Ala was analyzed in the same manner. These results are shown in Table 3.

TABLE 3

| | | | #1 | #2 | #3 | #4 | #5 | Average |
|---|---|---|---|---|---|---|---|---|
| 1 | a | Theoretical value | 20.80997 | | | | | |
| Fmoc-Ala | b | $^{16}O$ | 20.9302 | 20.9642 | 21.4555 | 22.6109 | 21.6341 | 21.519 |
| 2 | a | Theoretical value | 10.00187 | | | | | |
| Ala-Val | b | $^{16}O$ | 11.3917 | 11.2128 | 10.8295 | 10.8066 | 10.6185 | 10.972 |
| 3 | a | $^{17}O$ | 46.2628 | 46.1208 | 48.0115 | 48.4230 | 47.4903 | 47.262 |
| Fmoc-Ala | b | Theoretical | 20.27231 | 20.18225 | 21.36531 | 21.6182 | 21.0427 | 20.9 |
| 4 | A | $^{17}O$ | 24.1342 | 23.8455 | 23.6789 | 23.6108 | 23.5392 | 23.762 |
| Ala-Val | b | Theoretical | 12.3868 | 12.1652 | 12.0369 | 11.9842 | 11.9289 | 12.1 |

In Table 3, 1-4 represent the values for:
1. unlabeled Fmoc-Ala (control),
2. unlabeled Ala-Val (control),
3. $^{17}O$-labeled Fmoc-Ala (the present invention),
4. $^{17}O$-labeled Ala-Val (the present invention).

As shown in Table 1, $^{13}C$, $^{2}H$, $^{15}N$ and $^{17}O$ exist in a certain ratio as natural isotopes of C, H, N and O. The theoretical value in 1-a (20.810) and the theoretical value in 2-a (10.002) in Table 3 represent the theoretical values of the area ratio between the first isotopic peak and the second isotopic peak calculated from the natural isotopic abundances of (unlabeled (control)) Fmoc-Ala and (unlabeled (control)) Ala-Val. For example, 10.0 in 2-a is the theoretical value of the intensity ratio calculated by using "3x [natural isotopic abundance of $^{17}O$ (0.038)/natural isotopic abundance of $^{16}O$ (99.762)]" when the labeling rate x=0 in Formula 1 above. The averages of peak area ratios shown in 1-b and 2-b approximately agreed with the theoretical values.

3-a and 4-a in Table 3 represent measured area ratios between the first isotopic peak and the second isotopic peak for the $^{17}O$-labeled Fmoc-Ala and Ala-Val of the present invention, and the labeling rates calculated from these values are shown in 3-b and 4-b.

As shown in chemical formula 2 below, Fmoc-Ala may be labeled with $^{17}O$ at either one of two oxygen atoms in the carboxyl group. If this labeling method is repeated multiple times, both may be labeled with $^{17}O$. However, Ala-Val can be labeled with $^{17}O$ at only one oxygen atom from Fmoc-Ala.

[Formula 2]
A. Labeling of Fmoc-Ala

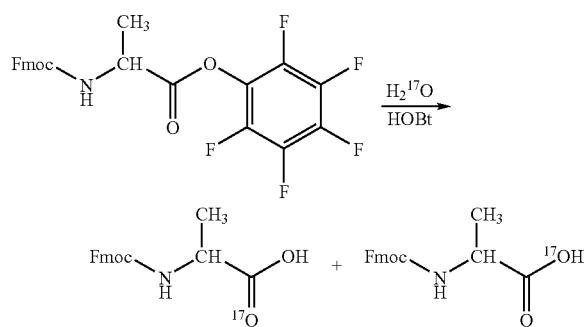

B. Labeling of Ala-Val

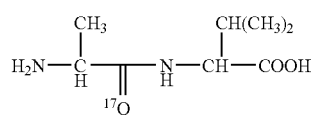

Example 3

$^{17}O$ MAS NMR Spectroscopy of Ile[$^{17}O$]

$^{17}O$ MAS NMR was performed on free Ile[$^{17}O$] prepared by the procedure of Example 1. $^{17}O$ MAS NMR spectroscopy is shown in FIG. 2.

Specifically, analysis was performed using an Infinity 400 NMR spectrometer available from Chemagnetics at resonant frequencies of oxygen and proton of 54.207 MHz and 399.88 MHz, respectively. A powdered sample was packed into a zirconia rotor and analyzed at room temperature. The rotation frequency of the sample was 12 kHz. $H_2O$ was used as a standard for chemical shift and for establishing RF intensity. The cycle time was 5 seconds.

Figure 2:
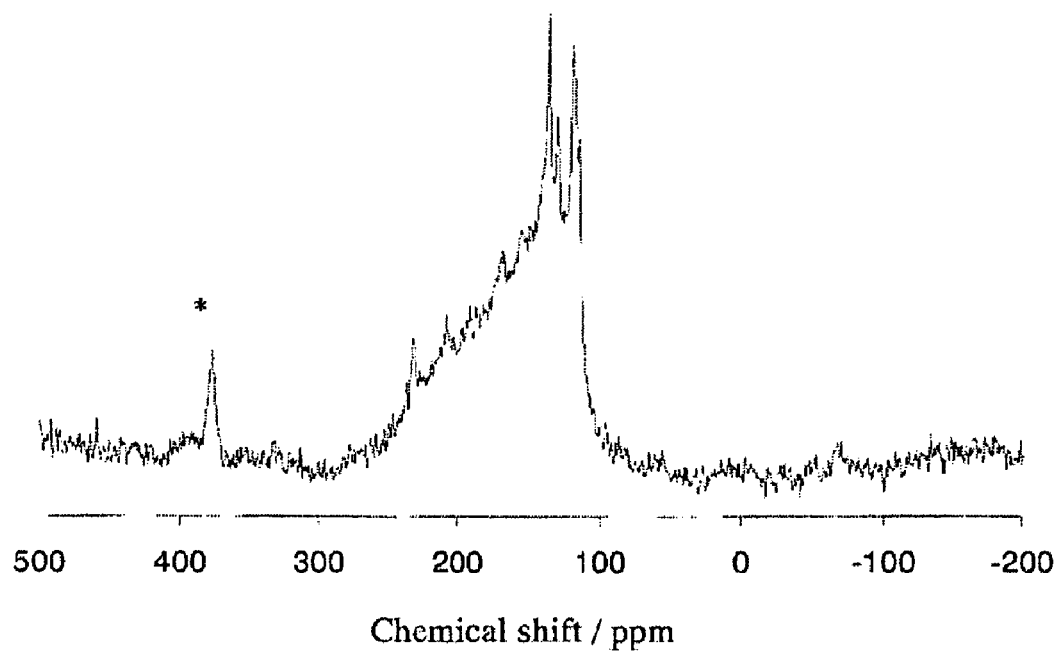
FIG. 2 shows $^{17}O$ MAS NMR spectroscopy of Ile[$^{17}O$]. The abscissa shows chemical shift in ppm.

The spectrum in FIG. 2 is a powder pattern basically composed of two components, $^{17}OH$ and C=$^{17}O$. The asterisk in FIG. 2 shows a signal from the zirconia rotor ($ZrO_2$).

Example 4

No Racemization of Amino Acids Occurs During Labeling by the Labeling Methods of the Present Invention In the present example, it was shown that amino acids obtained by the methods of the present invention were not isomerized during labeling.

Preparation of a Sample
(1) In a 0.1 M aqueous acetate solution was dissolved 10 mg of the $^{17}O$-valine obtained in Example 1.
(2) In 10 mL of methanol were dissolved 100 mg of N-acetyl-L-cysteine (Ac-Cys) and 100 mg of o-phthalaldehyde (OPTA).
(3) In 10 mL of water was dissolved 61.4 mg of boric acid and the solution was adjusted to pH 6.5 with sodium hydroxide.
(4) 100 μL of (1) and 20 μL of (2) and 100 μL of (3) were mixed, and the mixture was allowed to stand at room temperature for 5 minutes.
(5) An HPLC column was loaded with 100 μL of the mixed solution.
HPLC Conditions
Column: YMC Hydrosphere C18 (HS12S05-2546WT)
Solvent: isocratic with (A) phosphate buffer (1/15 mol/l, pH=6.4), (B) methanol at (A):(B)=54:46
Flow rate: 1.0 mL/min
Detection wavelength: 340 nm.
Results
The $^{17}O$-valine obtained in Example 1 was reacted with o-phthalaldehyde (OPTA) and N-acetyl-L-cysteine (Ac-Cys), and the reaction product was subjected to high-speed liquid chromatography (HPLC) (see Nimura, N., et al. J. Chromatogr., 402, 387, 1987). The results are shown in FIG. 3.

Figure 3:
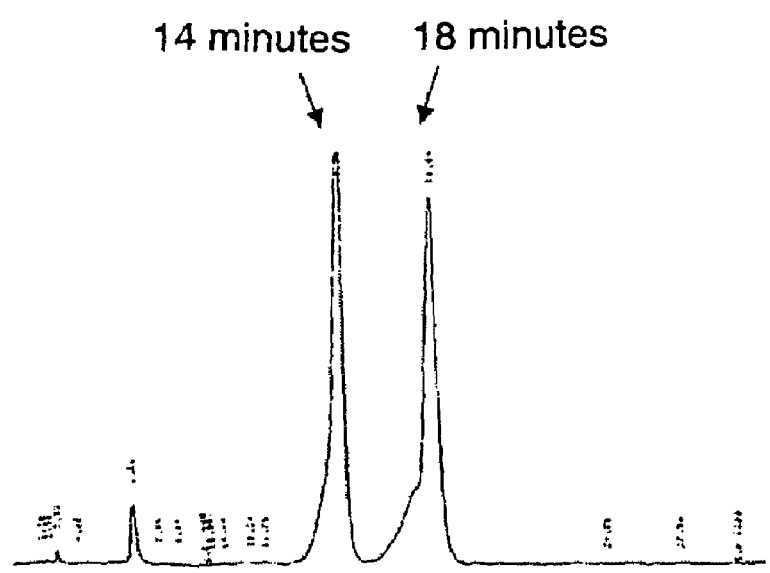
FIG. 3 shows HPLC patterns of diastereomer derivatives formed from OPTA, AcCys and DL-valine or $^{17}O$-valine. In the derivative from DL-valine shown in FIG. 3a, two peaks were observed in the HPLC pattern (left peak 14 minutes; right peak 18 minutes). In the derivative from $^{17}O$-valine shown in FIG. 3b, only a single peak was observed.
Figure 3:
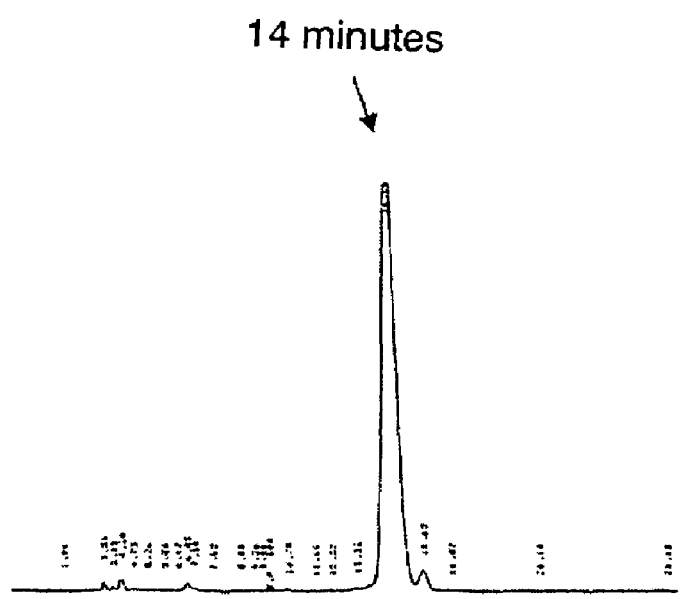

In FIG. 3, two equivalent peaks were observed for DL-valine used as a control (FIG. 3a), in contrast to $^{17}$O-valine showing a single peak derived from the L-isomer (FIG. 3b). The starting material of the $^{17}$O-valine obtained in Example 1 was Fmoc-L-valine pentafluorophenyl ester, showing that no isomerization (racemization) occurred during the labeling reaction of the present invention.

Example 5

Preparation of Labeled Fmoc-L-(O-tert-butyl)serine

In the present example, labeled Fmoc-L-(O-tert-butyl)serine was prepared.

Specifically, 1.260 g of Fmoc-L-(O-tert-butyl)serine N-hydroxysuccinimide ester (Novabiochem (Darmstadt, Germany)) and 450 mg of anhydrous HOBt were dissolved in 4.0 mL of anhydrous THF. Immediately after then, 200 μL of $H_2^{17}O$-enriched water (labeling rate 20.3%) was added, and the mixture was stirred at room temperature for 4 to 5 days. After the reaction has been completed, the reaction mixture was evaporated to dryness under reduced pressure to give a white product. The crude product was purified by chromatography on silica gel (100:2 (v/v) ethyl acetate:acetic acid) to give labeled Fmoc-L-(O-tert-butyl)serine.

The results of solution NMR and mass spectrometry of the product agreed with the calculated values. The labeling rate with $^{17}$O was identified as 20.0%.

The present example showed that N-hydroxysuccinimide esters are also useful as activated esters in the methods of the present invention. Moreover, one of characteristics of an embodiment of the present invention is that strongly acidic conditions are not used. In the present example, even a protecting group that can be removed under acidic conditions was shown to remain when it was attached to an amino acid. This is useful because the side chain need not be protected again when the amino acid obtained by the present example is used for chemical peptide synthesis (including solid-phase peptide synthesis), for example.

The invention claimed is:

1. A method for labeling one or two oxygen atom(s) in a carboxyl group of a carboxyl-containing compound with an oxygen isotope selected from oxygen-17 ($^{17}$O) or oxygen-18 ($^{18}$O), comprising reacting an activated ester of the carboxyl-containing compound (carboxylic acid) with $H_2^{17}O$ or $H_2^{18}O$ in the presence of an activator that is a coupling reagent or reaction-promoting additive in peptide synthesis.

2. The labeling method of claim 1 wherein the oxygen isotope is oxygen-17 ($^{17}$O).

3. The labeling method of claim 1 wherein the activator is a triazole derivative or tetraalkyluronium derivative.

4. The labeling method of any one of claims 1, 2 and 3 wherein the activator is 1-hydroxy-1H-benzotriazole or 6-chloro-1-hydroxy-1H-benzotriazole.

5. The labeling method of claim 1 wherein the activated ester is an ester selected from pentafluorophenyl esters, paranitrophenyl esters, 2,4,6-trichlorophenyl esters, and N-hydroxysuccinimide esters.

6. The labeling method of claim 1 wherein the carboxyl group to be labeled with an oxygen isotope is a carboxyl group in a biological component or a biological component-related molecule selected from the group consisting of amino acids, peptides, proteins, sugars, oligosaccharides, polysaccharides, glycoproteins, fatty acids, lipids, glycolipids, proteoglycans, cholesterols and steroids.

7. The labeling method of claim 1 wherein the carboxyl group to be labeled with an oxygen isotope is a carboxyl group in an amino acid, peptide or protein, and the amino group in the amino acid or the terminal amino group or side chain amino group in the peptide or protein is protected with a protecting group.

8. The labeling method of claims 7 wherein the protecting group is selected from the group consisting of 9-fluorenylmethoxycarbonyl, t-butyloxycarbonyl, benzyloxycarbonyl and 4-methoxybenzyloxycarbonyl groups.

9. The labeling method of claim 1 wherein the activated ester of a carboxylic acid is reacted with $H_2^{17}O$ or $H_2^{18}O$ under conditions of room temperature to 50° C.

10. The labeling method of claim 1 wherein the activated ester of a carboxylic acid is reacted with $H_2^{17}O$ or $H_2^{18}O$ under conditions excluding strongly acidic conditions or alkaline hydrolysis.

11. A process for preparing a synthetic peptide labeled with an oxygen isotope selected from oxygen-17 ($^{17}$O) or oxygen-18 ($^{18}$O) at the oxygen atom in the peptide bond, comprising:
   1) reacting an activated ester of an amino acid with $H_2^{17}O$ or $H_2^{18}O$ in the presence of an activator that is a coupling reagent or reaction-promoting additive in protein synthesis; and
   2) reacting the carboxyl group in the labeled amino acid with the N-terminal amino group of an amino acid or peptide bound to a solid phase.

12. A process for preparing a labelled amino acid labeled with an oxygen isotope selected from oxygen-17 ($^{17}$O) or oxygen-18 ($^{18}$O) at one or two oxygen atom(s) in the carboxyl group, comprising:
   1) reacting an activated ester of an amino acid protected with a protecting group at a terminal amino group with $H_2^{17}O$ or $H_2^{18}O$ in the presence of an activator that is a coupling reagent or reaction-promoting additive in protein synthesis; and
   2) removing the protecting group from the resulting labeled amino acid having the protecting group.

* * * * *